(12) United States Patent
Ali et al.

(10) Patent No.: US 11,504,463 B2
(45) Date of Patent: Nov. 22, 2022

(54) SYSTEMS AND METHODS FOR VERIFYING THAT A BIOLOGICAL PRODUCT IS READY FOR TREATMENT

(71) Applicant: Fenwal, Inc., Lake Zurich, IL (US)

(72) Inventors: Zahra R. Ali, Chicago, IL (US); Katherine N. Radwanski, Highland Park, IL (US)

(73) Assignee: Fenwal, Inc., Lake Zurich, IL (US)

( * ) Notice: Subject to any disclaimer, the term of this patent is extended or adjusted under 35 U.S.C. 154(b) by 499 days.

(21) Appl. No.: 16/737,082

(22) Filed: Jan. 8, 2020

(65) Prior Publication Data

US 2020/0222620 A1 Jul. 16, 2020

Related U.S. Application Data

(60) Provisional application No. 62/790,798, filed on Jan. 10, 2019.

(51) Int. Cl.
*A61M 1/36* (2006.01)

(52) U.S. Cl.
CPC ........ *A61M 1/3683* (2014.02); *A61M 1/3696* (2014.02); *A61M 2202/0427* (2013.01); *A61M 2202/0439* (2013.01); *A61M 2205/051* (2013.01); *A61M 2205/50* (2013.01); *A61M 2230/207* (2013.01)

(58) Field of Classification Search
CPC combination set(s) only.
See application file for complete search history.

(56) References Cited

U.S. PATENT DOCUMENTS

| 5,360,542 | A | 11/1994 | Williamson, IV et al. |
| 6,027,657 | A | 2/2000 | Min et al. |
| 7,433,030 | B2 | 10/2008 | Waldo et al. |
| 9,399,093 | B2 | 7/2016 | Min et al. |
| 2007/0083144 | A1 | 4/2007 | Petrie |
| 2014/0370491 | A1 | 12/2014 | Radwanski |
| 2017/0028121 | A1 | 2/2017 | Manzella et al. |
| 2017/0029776 | A1 | 2/2017 | Cork et al. |
| 2018/0147306 | A1 | 5/2018 | Crawley et al. |

FOREIGN PATENT DOCUMENTS

WO WO 2000/074731 A1 12/2000

OTHER PUBLICATIONS

Extended European Search Report dated Sep. 8, 2020 for European Patent Application No. 20150655.7 (EP Patent No. 20150655).

*Primary Examiner* — Dirk R Bass
(74) *Attorney, Agent, or Firm* — Cook Alex Ltd.

(57) ABSTRACT

Systems and method for verifying the timely placement of a container of biolocal cells or fluid within a treatment chamber of a biological fluid treating device are disclosed. The systems and methods utilize a sensor that detects the presence of a container at an appropriate and pre-determined time and, optionally, detects the weight of the container and cells.

21 Claims, 6 Drawing Sheets

SYSTEMS AND METHODS FOR VERIFYING THAT A BIOLOGICAL PRODUCT IS READY FOR TREATMENT

CROSS-REFERENCE TO RELATED APPLICATION

This application claims the benefit of and priority to U.S. Provisional Patent Application Serial No. 62/790,798, filed on Jan. 10, 2019, the disclosure of which is incorporated herein by reference in its entirety.

FIELD OF THE DISCLOSURE

The present disclosure is directed to the treatment of a biological fluid or product. More particularly, the present disclosure is directed to systems and methods for treating a biological fluid in an irradiation device. Even more particularly, the present disclosure is directed to systems and methods for verifying that the biological fluid is present and ready for treatment with light within the irradiation device, that the dose of light is appropriate for the volume or weight of the biological fluid and if not, adjusting the dose of light accordingly.

BACKGROUND

Biological fluids may be subjected to treatment as part of a therapy. An irradiation device is particularly useful in certain treatments of biological fluids. As used herein, biological fluid refers to any fluid that is found in or that may be introduced into the body including, but not limited to, blood and blood products. As used herein, "blood product" refers to whole blood or a component of whole blood such as red blood cells, white blood cells, platelets, plasma or a combination of one or more of such components that have been separated from whole blood.

For example, an irradiation device may be used in the treatment of a blood product that has been combined with a photochemical agent for activation when subjected to light. Such photochemical agents are used, for example, in the inactivation of viruses, bacteria, and other contaminants (collectively referred to herein as "pathogens"). Photochemical agents are also used in the treatment of mononuclear cells, such as white blood cells. In the treatment of mononuclear cells, the activated agent targets the mononuclear cell itself as part of a treatment of a disease or a side effect of a mononuclear cell therapy. One such treatment of mononuclear cells (MNCs) is referred to as extracorporeal photopheresis.

In an extracorporeal photopheresis (ECP) procedure, collected MNCs are treated with a combination of UV-A light and 8-Methoxypsoralen (8-MOP). If delivered in the right dosage, this combination causes an apoptotic response in the treated MNCs. This response is the desired treatment for conditions such as Cutaneous T-Cell lymphoma (CTCL), Acute and chronic Graft versus host disease (GvHD), and Heart and Lung transplant rejection. During an extracorporeal photopheresis procedure, an MNC collection is carried out to collect MNCs to be treated. Then, 8-MOP is injected or otherwise delivered into the treatment container (which may be the MNC collection container used during MNC collection procedures) and this mixture is photoactivated in an irradiation device with UV-A light. The treated cells are then re-infused into the patient. Systems and methods for performing ECP are described in U.S. Patent Application Publication US2014/0370491 and U.S. Pat. No. 9,399,093, all of which are incorporated by reference herein in their entireties. Examples of irradiation devices useful in carrying out ECP procedures are described in U.S. Patent Application Publications US 2017/0028121, US 2017/0029776 and US 2018/0147306, all of which are also incorporated by reference herein in their entireties.

The irradiation device typically includes a treatment chamber (e.g., an irradiation chamber) and one or more light sources and a UV sensor(s) that measure the amount of light being delivered to the biological fluid, and a controller that controls how long the UV-A light sources remain activated based on the intensity of UV-A light sensed.

In the treatment of biological cells, such as in photopheresis, for the cells to generate the desired therapeutic effect, the cells must have been sufficiently exposed to radiation or other treatment. Thus, it would be desirable to provide a system and method wherein the operator could verify that the biological cells have, in fact, been placed or located in the treatment chamber of the device. In addition, it would be desirable for the operator to be able to verify the amount (volume, weight) of the biological fluid/cells present in the treatment chamber and take into account changes in the amount that may have occurred in earlier phases of the procedure. Furthermore, it would be desirable if the system could adjust the light dose administered based on the actual volume or weight of the cells to be treated at the time of treatment (as compared to a calculated or estimated value). Finally, it would be desirable for the system to recognize if the container of biological cells has been inadvertently or prematurely loaded into the treatment chamber before it is "treatment-ready."

SUMMARY

In one aspect the present disclosure is directed to a system for treating a biological fluid with light. The system includes an irradiation device with one or more light sources and an irradiation chamber for receiving a container of biological fluid. The system further includes a detector for detecting that a container is present in the irradiation chamber. The system further includes a controller configured to receive information from the detector and verifying that said biological fluid is present and ready for treatment.

In another aspect, the present disclosure is directed to a method for verifying the presence of a container of biological fluid within a treatment chamber of a biological fluid treating device at a pre-determined, "treatment-ready" time. The method includes placing a container of biological fluid within a treatment chamber of a biological fluid treating device and detecting the weight of the container of biological fluid. The method further includes, optionally, comparing the detected weight to a pre-determined weight or weight range for a treatment. The method includes determining whether the biological fluid is treatment-ready based on the comparison.

DETAILED DESCRIPTION OF THE EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
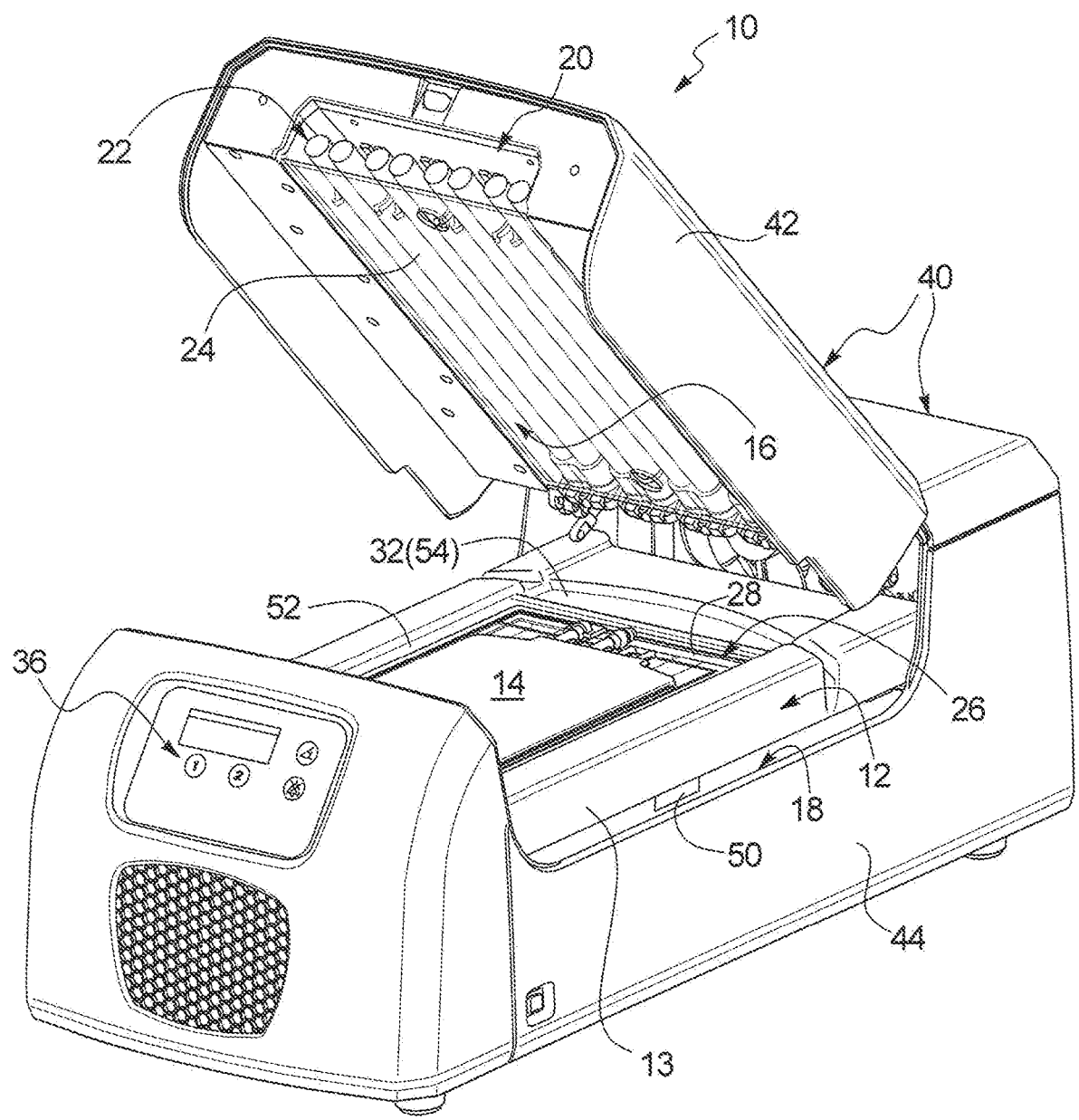
FIG. 1 is a perspective view of an embodiment of a device used to irradiate a biological fluid in a biological fluid container.
Figure 2:
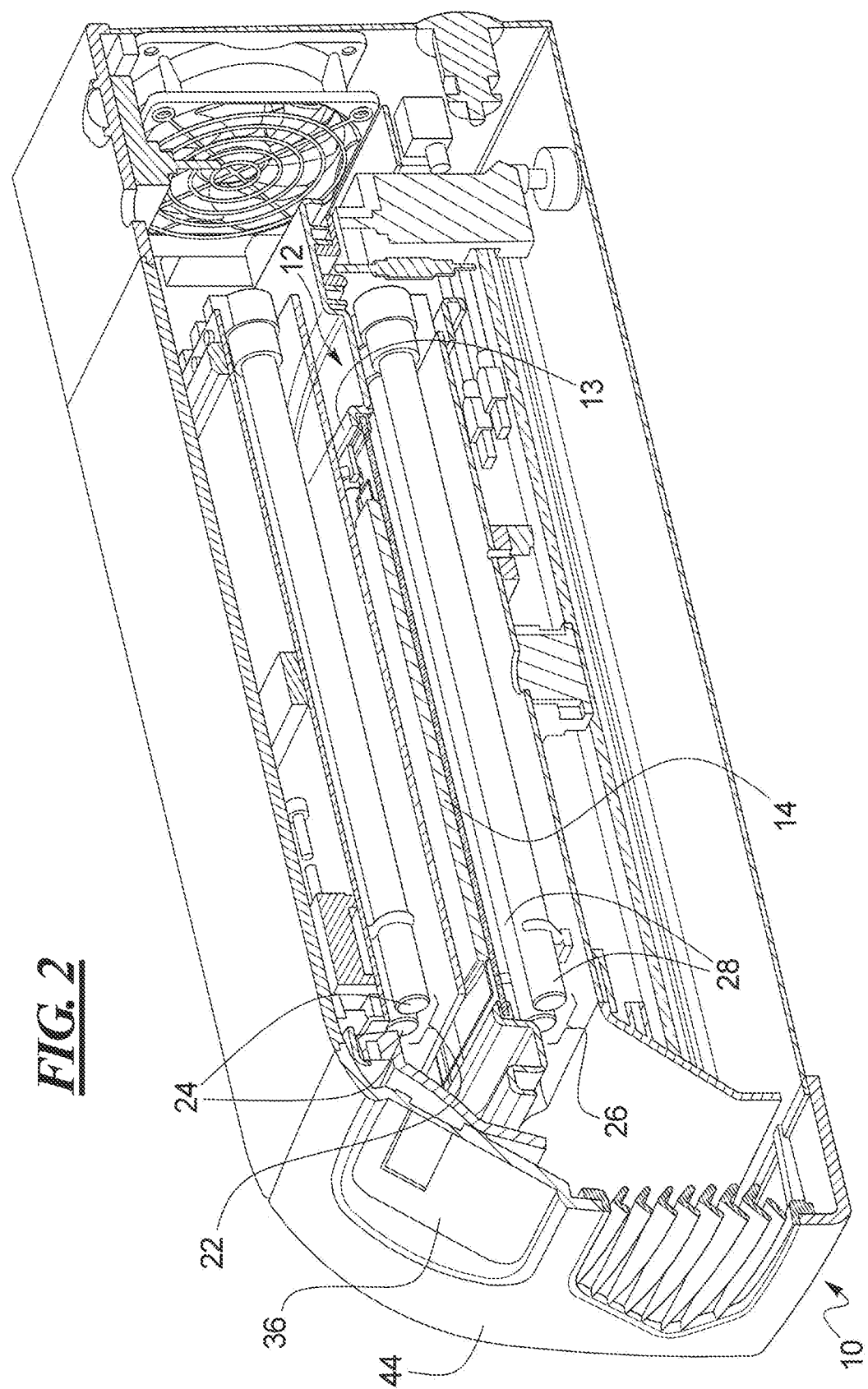
FIG. 2 is a perspective view, in cross section, of the irradiation device of FIG. 1.

As illustrated in FIG. 1, an irradiation device 10 include a fluid treatment/irradiation chamber 12 defined at least in part by or including a tray 13. Tray 13 may include at least one recess or pocket 14 configured to receive one or more biological fluid container(s) 14. Fluid treatment chamber 12 includes opposing first and second sides 16, 18. As illustrated in FIGS. 1 and 2, device 10 also includes at least one light source 20 disposed adjacent at least one of first and second sides 16, 18 of fluid treatment/irradiation chamber 12. Light source 20 may include, for example, a first array 22 with a plurality of light sources 24 disposed on first side 16 of fluid treatment chamber 12 and a second array 26 with a plurality of light sources 28 disposed on second side 18 of fluid treatment chamber 12 (FIG. 2). According to an embodiment of the present disclosure, light sources 24, 28 are similar in structure and operation, and provide electromagnetic radiation in the ultraviolet portion of the spectrum (e.g., UVA). An alternative device is described in U.S. Pat. No. 7,433,030, the contents of which are incorporated by reference herein in its entirety. Device 10 may include an agitator, as shown and described in U.S. Patent Application Publication US 2017/0029776, previously incorporated by reference, coupled to tray 13 to move at least a part of tray 13 with an oscillatory motion. Agitator may include a motor in combination with a linkage (such as a rotating cam), the linkage coupling the motor to tray 13.

Figure 4:
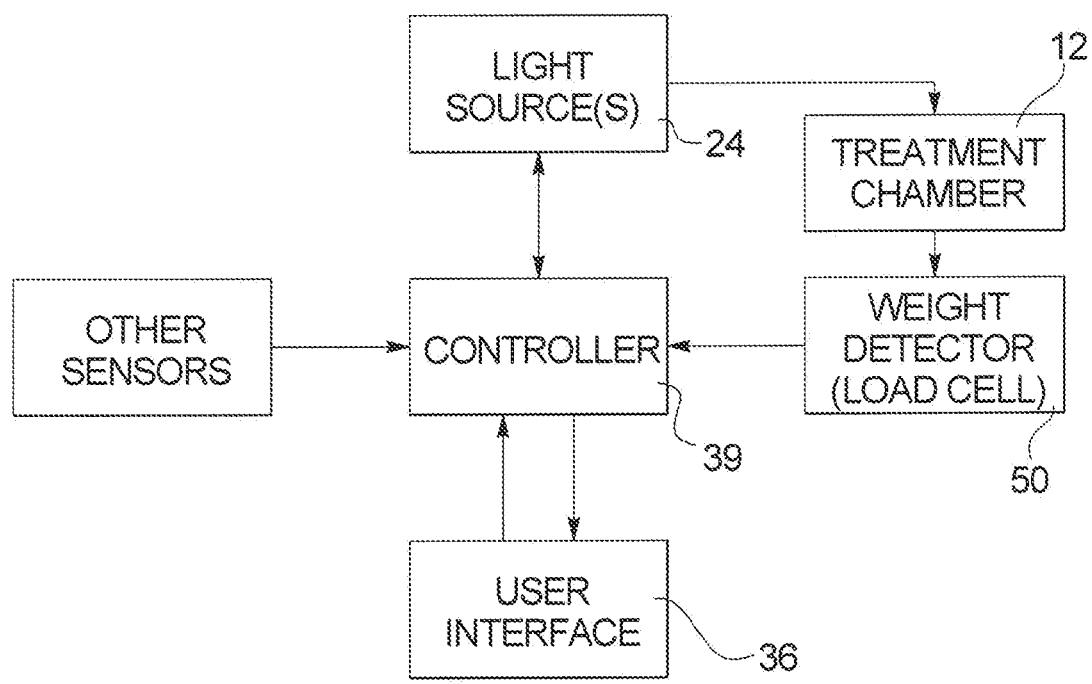
FIG. 4 is a block diagram of an embodiment of the electronic components of the irradiation device of FIG. 1 or ECP system generally.

As further shown in FIG. 1, device 10 may also include a housing 40 in which fluid treatment chamber 12 is defined, and in which light source 20, agitator, and other components of device 10, including one or more sensors and controller 39 (described in greater detail below and schematically shown in FIG. 4) are disposed. While FIG. 1 illustrates an embodiment of housing 40 including a lid 42 that may be moved pivotally relative to a base 44 to open housing 40 and permit access to fluid treatment chamber 12, it will be recognized that according to other embodiments of device 10, housing 40 may instead include a sliding drawer that permits access to tray 13.

One or more sensors (e.g., one or more of a UV sensor, a hematocrit sensor, a viscosity detector, a temperature sensor, an air detector, and a density detector) are disposed within the fluid treatment chamber 12 for measuring a condition of the biological fluid in the fluid container 14. Preferably, the sensors are mounted within or near the fluid treatment chamber in proximity to the fluid being treated. According to different embodiments, a single sensor may be provided, or a plurality of sensors may be provided to measure the various sensed conditions.

Figure 3:
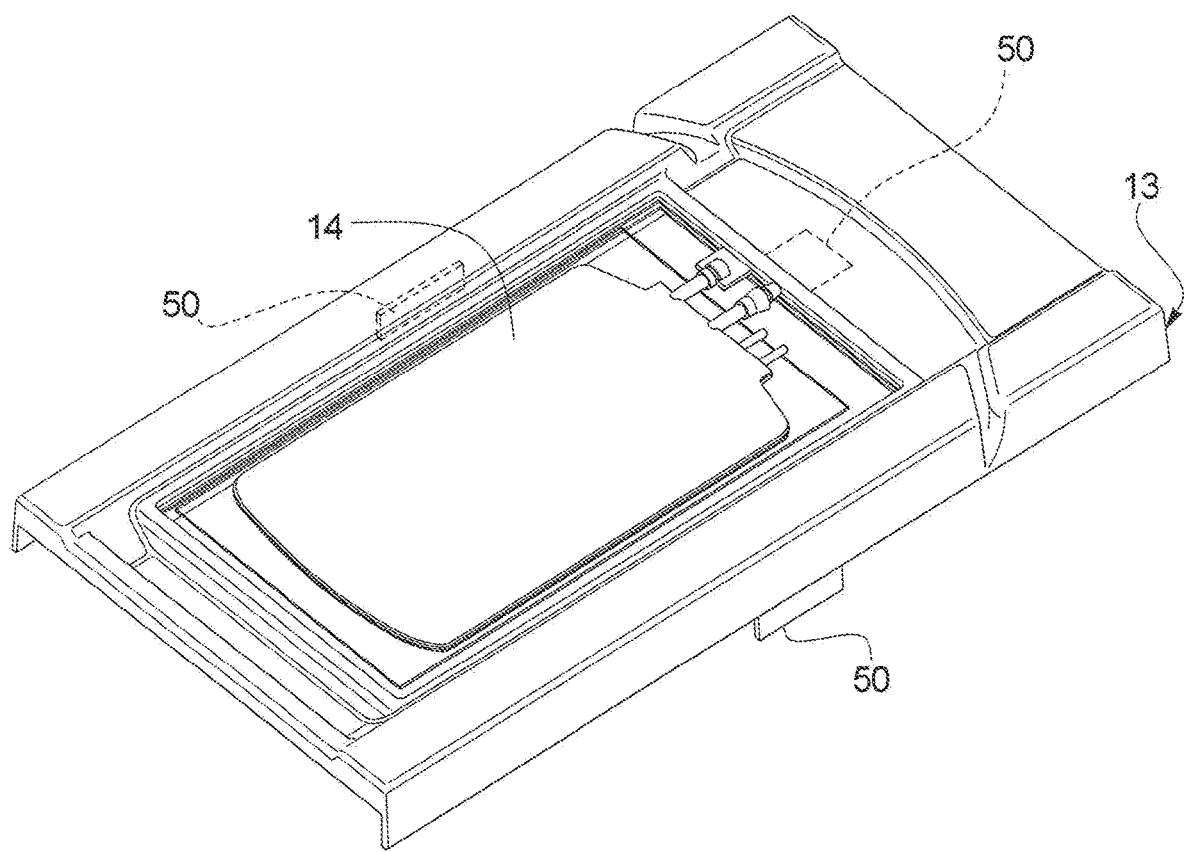
FIG. 3 is a top perspective view of an embodiment of a tray for use with the device of FIG. 1.

In accordance with the present disclosure, device 10 may further include one or more sensor(s) 50 for detecting the presence and/or weight of the container of biological cells that have been placed within tray 13/treatment chamber 12, as shown in FIGS. 1 and 3. Sensor 50 may be a load cell configured to detect a change in the weight within tray 13/chamber 12 and generate an electrical signal in response to such weight change. Sensor(s) 50 is preferably located in proximity to or associated with tray 13 as shown in FIGS. 1 and 3 and schematically in FIG. 4. In one embodiment a pair of sensors may be located at opposite sides (or ends) of tray 13 and preferably along the bottom edge thereof, as shown in FIG. 3. Alternatively, sensor 50 may be located at an end as also shown on phantom lines in FIG. 3. While tray may include a single sensor 50, alternatively, a pair of sensors along the bottom edge of each side may be provided. Including a pair of sensors may be advantageous in that it would provide two weight readings, thereby ensuring a more accurate overall weight determination. Sensor 50 generates an electrical signal that is transmitted to and received by controller 39.

Controller 39 may take the form of one or more electrical components or circuits, and comprises a processor and an associated memory according to one embodiment. According to such embodiment, the processor may be programmed to carry out any of the actions that controller 39 is described as being configured to perform below. The instructions by which the processor is programmed may be stored on the memory associated with the processor, which memory may include one or more tangible non-transitory computer readable memories, having computer executable instructions stored thereon, which when executed by the processor, may cause the one or more processors to carry out one or more actions.

In one embodiment, controller 39 may be pre-programmed to receive a signal from sensor 50 as an indication of the presence (or absence of) a container in tray 13 and/or treatment chamber 12 at selected times of a photoactivation procedure. For example, when the biological fluid is ready for treatment and is placed inside tray 13/treatment chamber 12, sensor 50 will detect a change in weight and send a signal to controller 39 verifying that a container of cells/fluid is present. Once the presence of a container of biological fluid has been verified, the system may automatically generate a signal to the operator that the photoactivation procedure may commence. On the other hand, if no signal is received by controller 39 from sensor 50 when it otherwise should be (in the sequence of a procedure), or if the signal generated is one that otherwise indicates that tray 13 is empty, the system under the direction of controller may generate an alert that no container is present in the tray/treatment chamber 12. This will allow the operator to take any necessary remedial action, including without limitation, pausing the procedure, loading container 14 etc.

Additionally, the system may alert the operator when a container of biological fluid or cells has been inadvertently or prematurely placed in tray 13 and/or treatment chamber 12. Premature placement of the biological fluid container in tray 13/treatment chamber 12 may cause the biological fluid to be exposed to (additional) radiation during warm up or calibration of the light sources 24, 28. Having been exposed to this unintended radiation in addition to the pre-determined light dose of the photoactivation treatment, the cells may be damaged and rendered unsuitable for return to the patient. Thus, in accordance with the present disclosure, sensor 50 will detect any weight change at the tray 13/treatment chamber 12 and will signal controller 39 accordingly. If the timing of the signal transmission does not correspond with the pre-determined sequence of steps in a procedure, the system may generate an alert.

For example, where sensor 50 detects the presence of a container within tray 13/treatment chamber 12 prior to bulb warm-up and/or calibration, it may generate an alert and pause or terminate the procedure to allow the operator to remedy or otherwise address the alert condition. Similarly, other inadvertent or premature placements of the biological fluid container within tray 13/chamber 12 may also be detected by sensor 50, such as placement of container 14 in tray 13 prior to the introduction of the photoactive agent with the biological fluid or cells, or prior to dilution of the cells with a conditioning fluid that may be desired to arrive at the appropriate hematocrit. In other words, the controller may be pre-programmed to verify the presence of a container in the tray 13/treatment chamber 12, and that the cells or fluid are "treatment-ready."

In addition to verifying the presence of a "treatment-ready" container of cells/fluid, controller 39 may be pre-programmed to verify that the selected dose of light is appropriate for the effective treatment of the particular container of biological fluid. Typically, the desired light dose may be determined by taking into account the particular characteristics of the biological fluid to be treated such as, but not limited to, the composition of the particular biological fluid. For example, as noted above, where the biological fluid is mononuclear cells (MNCs) undergoing a photodynamic therapy, the characteristics that may enter into determining the desired light dose may include the concentration of the cells, the hematocrit of the cellular product, the volume of the cellular product, the type of photoactive agent and the like. The controller may then verify the duration of the treatment based on the expected output of the light sources 24, 28 within each array 22, 26 for the given biological fluid.

In accordance with the present disclosure, the controller, based on the weight of the container as detected by sensor 50 may also take into account such weight or volume of the biological cells/fluid and adjust the light dose by, for example, adjusting the duration of the exposure, the light intensity or both.

Thus, sensor 50 communicates with controller 39 and not only transmits the detected presence of a container but also, optionally, the detected weight of the biological fluid container. Detection of the container weight once it is placed in the tray 13 at the appropriate i.e., "treatment-ready" time, provides a reliable quantification (e.g., volume, weight) of the cells that are about to be treated as such placement s one of the last events before irradiation of the cells. Prior to this step, volume changes to the collected cells may have occurred due to removal of some volume of cells for sampling, addition of the photoactivation agent, dilution or conditioning of the cells with saline or other fluid to arrive at the desired hematocrit, etc.

As noted above, the total amount of light energy to which the container of biological fluid is to be subjected during the irradiation cycle may be either preprogrammed into the controller or input by the operator through the user interface 36. The irradiation cycle may then be initiated, with the light sources 24, 28 being activated, thereby illuminating biological fluid container 14 in fluid treatment/irradiation chamber 12. The fluid container 14 is preferably oscillated by activating the agitator at the initial rate, thereby agitating biological fluid container 14 while biological fluid container 14 is illuminated.

Figure 5:
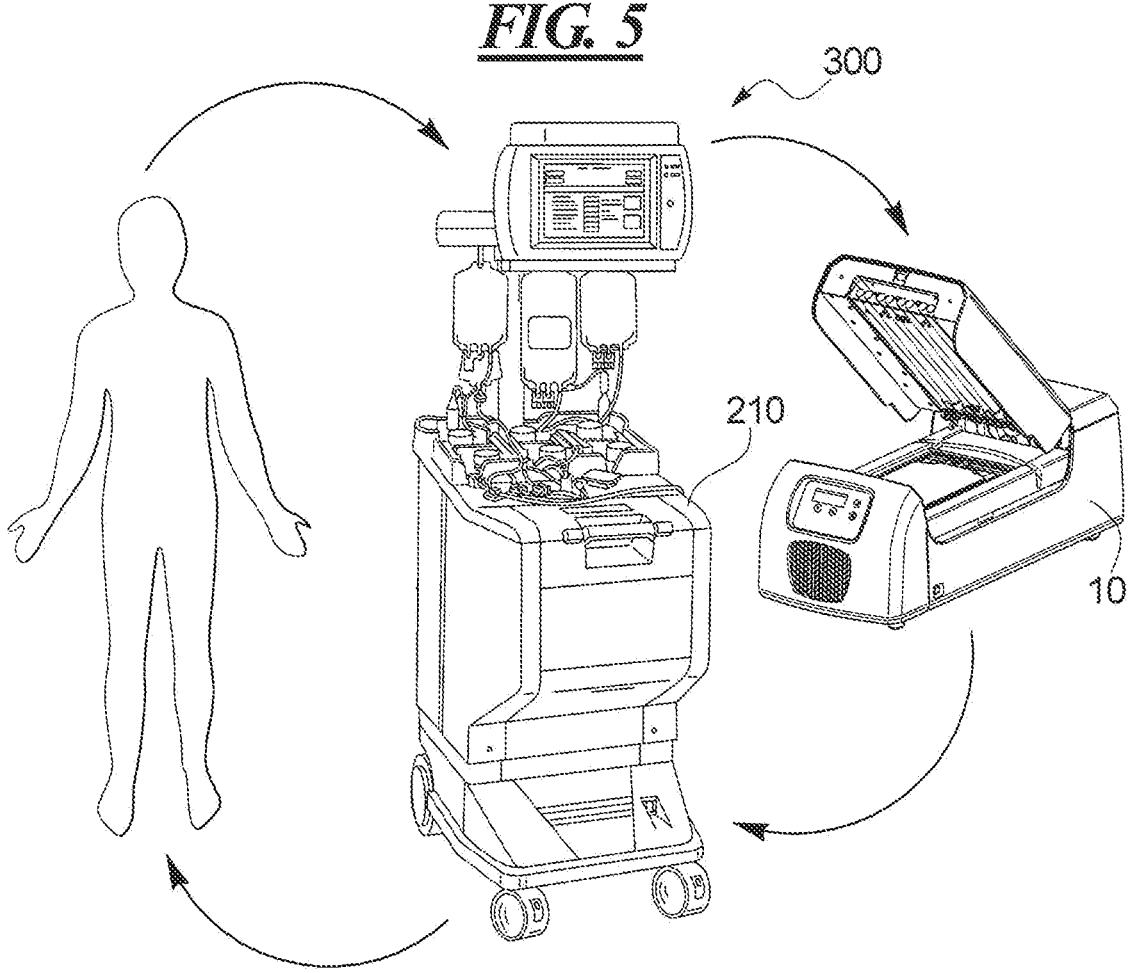
FIG. 5 is a diagram of an embodiment of a system including the irradiation device of FIG. 1 in combination with a cell separator.
Figure 6:
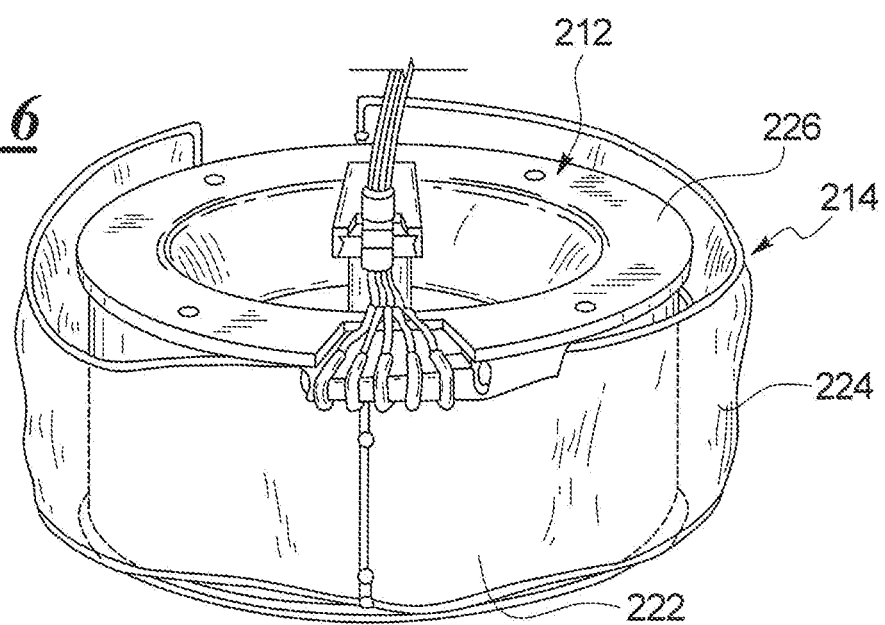
FIG. 6 is a perspective view of a processing container (separation chamber) of a processing set used with the separator of FIG. 5.
Figure 7:
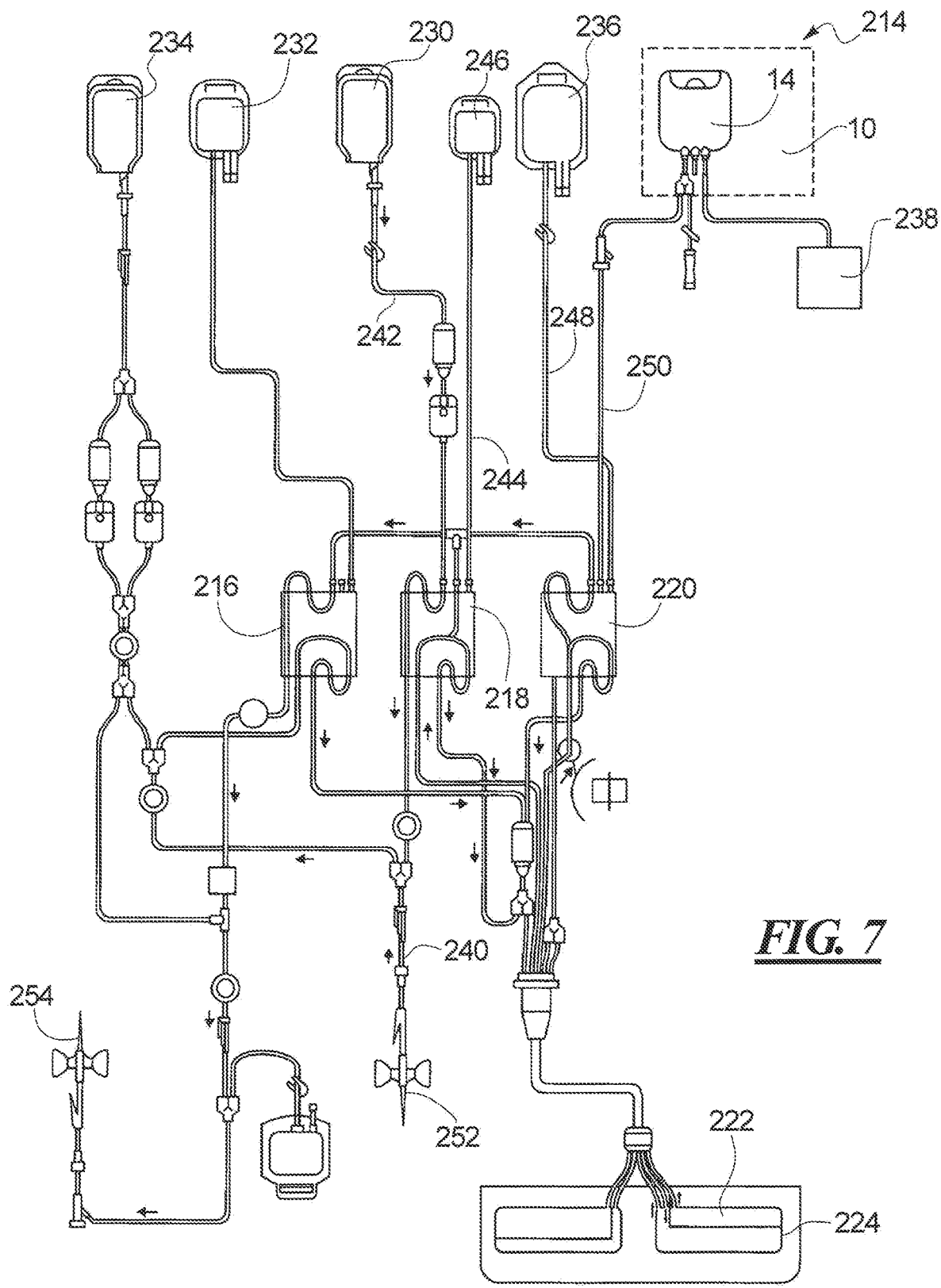
FIG. 7 is a diagram of a processing set for used with the separator of FIG. 7, including the processing container illustrated in FIG. 6.

While irradiation device 10 may be used as a stand-alone device, irradiation device 10 may also be used in conjunction with a cell separator 210 as part of a system 300, as illustrated in FIGS. 5-7. With reference to FIGS. 5-7, system 300 includes a cell separator 210 and irradiation device 10. Cell separator 210 would be configured to direct a biological fluid into a biological fluid container (e.g., container 14), and irradiation device 10 would include fluid treatment/irradiation chamber 12 configured to receive biological fluid container 14, as described above. The cell separator 210 may be an Amicus® Separator made and sold by Fenwal, Inc., of Lake Zurich, Ill., a subsidiary of Fresenius-Kabi of Bad Homburg, Germany. Mononuclear cell collections performed using a device such as the Amicus® are described in greater detail in U.S. Pat. No. 6,027,657, the contents of which is incorporated by reference herein in its entirety.

Briefly, FIGS. 5-7 show separator 210 in FIG. 5, a representative blood centrifuge 212 (defining part of the separator 210) with a portion of a fluid circuit 214 mounted thereon in FIG. 6, and the entire fluid circuit 214 in FIG. 7. Fluid circuit (also referred to as a processing set) 214 includes a plurality of processing fluid flow cassettes 216, 218 and 220 (see FIG. 7) with tubing loops for association with peristaltic pumps on device 210. Fluid circuit 214 also includes a network of tubing and pre-connected containers for establishing flow communication with the patient and for processing and collecting fluids and blood and blood components, as shown in greater detail in FIG. 9.

As illustrated in FIGS. 6 and 7, a separation chamber 222 is defined by the walls of a flexible processing container 224 carried within an annular gap defined by a rotating spool element 226 (see FIG. 6) and an outer bowl element (not shown). The processing container 224 takes the form of an elongated tube that is wrapped about the spool element 226 before use. The bowl and spool element 226 are pivoted on a yoke between an upright position and a suspended position, also not shown. In operation, the centrifuge 212 rotates the suspended bowl and spool element 226 about an axis, creating a centrifugal field within the processing chamber of container 224. Details of the mechanism for causing relative movement of the spool 226 and bowl elements as just described are disclosed in U.S. Pat. No. 5,360,542, the contents of which is also incorporated by reference herein in its entirety.

As seen in FIG. 7, the disposable processing set 214 may include flexible processing container 224, as well as a container 230 for supplying anticoagulant, a waste container 232 for collecting waste from one or more steps in the process for treating and washing mononuclear cells, a container 234 for holding saline or other wash or resuspension medium, a container 236 for collecting plasma, container 14 for collecting mononuclear cells from the operation discussed relative to FIG. 6 and, optionally, container 238 for holding a photoactivation agent or other device (such as a syringe for delivering the agent.

Container 14 is preferably pre-attached to with the disposable set 214. Alternatively, container 14 may be attached to set 214 by known sterile connection techniques, such as sterile docking or the like. With reference to FIG. 7, fluid circuit includes inlet line 240, an anticoagulant (AC) line 242 for delivering AC from container 230, an RBC line 244 for conveying red blood cells from chamber 222 of container 224 to container 246, a platelet-poor plasma (PPP) line 248 for conveying PPP to container 236 and line 250 for conveying mononuclear cells to and from separation chamber 222 and collection/illumination container 14. The blood processing set 214 includes one or more venipuncture needle(s) for accessing the circulatory system of the patient. As shown in FIG. 7, fluid circuit 214 includes inlet needle 252 and return needle 254. In an alternative embodiment, a single needle can serve as both the inlet and outlet needle.

Container 14 is suitable for irradiation by light of a selected wavelength. By "suitable for irradiation", it is meant that the walls of the container are sufficiently translucent to light of the selected wavelength. In treatments using UVA light, for example, container walls made of ethylene vinyl acetate (EVA) are suitable. Accordingly, container 14 in which the mononuclear cells are collected may serve both as the collection container and the irradiation container. Container 14 may be placed inside irradiation device 10 by the operator at the appropriate time, as discussed above, or may be placed inside the irradiation chamber of irradiation device 10 at the beginning of a procedure including the cell separation and prior to whole blood withdrawal. In the event that the container is placed in irradiation device at the beginning of a procedure (and prior to whole blood withdrawal), sensor 50 may detect changes in the weight of container 14 during the course of the ECP procedure. This allows the system to determine when transfer of the cells to container 14 is complete and, optionally, instruct the system (under the command of the controller 39) to energize light sources 24, 28 for treatment. In this case, sensor 50 would also monitor and record any earlier and additional exposure of container 14 to light (e.g., during self-checks and the like) and adjust the treatment parameters accordingly. Preferably container 14 remains integrally connected to the remainder of fluid circuit 214 during the entire procedure, thereby maintaining the closed or functionally closed condition of fluid circuit 214.

Fluid flow through fluid circuit 214 is preferably driven, controlled and adjusted by controller in cooperation with the valves, pumps, weight scales and sensors, including sensor 50, of device 210 and fluid circuit 214, the details of which are described in the previously mentioned U.S. Pat. No. 6,027,657. In this regard, automated control of the MNC collection and the irradiation treatment may be effectuated by the microprocessor-based controller of the respective separation device 210 and irradiation device 10 with some operator input for each device. Alternatively, operation of both separation device 210 and irradiation device 10 and the process steps carried out by each may be remotely controlled by a separate controller (e.g., a computer) that communicates with both.

Without limiting any of the foregoing, the disclosed device, method and system may include one or more of the aspects set forth below.

OTHER EXAMPLES

Aspects of the present subject matter described above may be beneficial alone or in combination with one or more other Aspects, as described below.

Aspect 1. A system for treating a biological fluid with light comprising: an irradiation device comprising one or more light sources and a an irradiation chamber for receiving a container of biological fluid; a detector for detecting that a container is present in said irradiation chamber; and a controller configured to receive information from the detector and verifying that the biological fluid is ready for treatment.

Aspect 2. The system of Aspect 1 wherein the controller is further configured to effect the commencement of treatment after the verification.

Aspect 3. The system of any one of Aspects 1 and 2 wherein said detector is configured to detect the weight of the container.

Aspect 4. The system of Aspect 3 method wherein the controller is configured to adjust a light dose to be delivered to the container of biological fluid based on the detected weight of the container.

Aspect 5. The system of any one of Aspects 1 through 4 wherein the controller is configured to determine if the weight of said container is within a pre-determined weight range.

Aspect 6. The system of any one of Aspects 1 through 5 wherein the controller is further configured to verify that the detected weight of the container has occurred at a pre-determined time.

Aspect 7. The system of Aspect 6 wherein the controller is configured to prevent irradiation of the container of biological fluid upon detection of the weight of the container when the detection occurs at other than said pre-determined time.

Aspect 8. The system of any one of Aspects 1 through 7 wherein the irradiation device includes a tray for receiving the container.

Aspect 9. The system of Aspect 8 wherein the detector is configured to detect the weight of the container received within the tray.

Aspect 10. The system of any one of Aspects 1 through 9 wherein the detector is associated with the tray.

Aspect 11. The system of any one of Aspects 6 through 7 wherein the controller is configured to prevent premature placement of the container in the irradiation chamber.

Aspect 12. A method for verifying the presence of a container of biological fluid within an treatment chamber of a biological fluid treating device at a pre-determined, treatment—ready time, the method including: placing a container of biological fluid within a treatment chamber of a biological fluid treating device; detecting the presence of the container of biological fluid by detecting a weight of the biological fluid; optionally comparing the detected weight to a pre-determined weight or weight range for a treatment; and determining whether the biological fluid is treatment-ready based on the comparison.

Aspect 13. The method of Aspect 12 further including treating the biological fluid when the detected weight substantially equals the pre-determined weight or is within the pre-determined weight range.

Aspect 14. The method of Aspect 12 including adjusting a treatment parameter when the detected weight does not substantially equal the pre-determined weight or is outside the predetermined weight range.

Aspect 15. The method of Aspect 12 comprising determining whether the biological fluid is treatment-ready by comparing the time of the detecting step relative to other events in a treatment.

Aspect 16. The method of Aspect 12 comprising detecting the weight of the container at a pre-selected time of a treatment.

Aspect 17. The method of any one of Aspects 12 through 16 wherein the treatment comprises a treatment of a biological fluid with light.

Aspect 18. The method of Aspect 17 including adjusting the duration of the light treatment in response to the detected weight of the container of biological fluid.

Aspect 19. The method of Aspect 17 including adjusting the intensity of said light in response to the detected weight of the container of biological fluid.

Aspect 20. The method of Aspect 17 including detecting the weight of the container of biological fluid to determine whether the biological fluid is treatment-ready.

Aspect 21. The method of Aspect 20 wherein detecting the weight of the container is an indication that the container has been prematurely placed in the treatment chamber.

Aspect 22. The method of any one of Aspects 12 through 21 further including generating an alert when the weight of the container does not substantially equal the pre-determined weight or is outside the predetermined weight range.

Aspect 23. The method of any one of Aspects 12 through 21 further including generating an alert when the container is not treatment ready or when the container has been prematurely placed in the treatment chamber.

The invention claimed is:

1. A system for treating a biological fluid with light comprising:
   a) an irradiation device comprising one or more light sources and an irradiation chamber for receiving a container of biological fluid;
   b) a detector for detecting that a container is present in said irradiation chamber wherein said detector is configured to detect the weight of said container; and
   c) a controller configured to receive information from said detector and verifying that said biological fluid is ready for treatment, wherein said controller is configured to adjust a light dose to be delivered to said container of biological fluid based on the detected weight of said container.

2. The system of claim 1 wherein said controller is further configured to effect the commencement of treatment after said verification.

3. The system of claim 1 wherein said controller is configured to determine if the weight of said container is within a pre-determined weight range.

4. The system of claim 1 wherein said controller is further configured to verify that the detected weight of said container has occurred at a pre-determined time.

5. The system of claim 4 wherein said controller is configured to prevent irradiation of said container of biological fluid upon detection of said weight of said container when said detection occurs at other than said pre-determined time.

6. The system of claim 1 wherein said irradiation device includes a tray for receiving said container.

7. The system of claim 6 wherein said detector is configured to detect the weight of said container received within said tray.

8. The system of claim 1 wherein said detector is associated with said tray.

9. The system of claim 4 wherein said controller is configured to prevent premature placement of said container in said irradiation chamber.

10. A method for verifying the presence of a container of biological fluid within a treatment chamber of a biological fluid treating device at a pre-determined, treatment-ready time, said method comprising:
    a) placing a container of biological fluid within a treatment chamber of a biological fluid treating device;
    b) detecting the presence of said container of biological fluid by detecting a weight of said biological fluid;
    c) optionally comparing the detected weight to a pre-determined weight or weight range for a treatment; and
    d) determining whether the biological fluid is treatment-ready based on said comparison; and
    e) adjusting a light dose in response to the detected weight of said container of biological fluid.

11. The method of claim 10 further comprising treating said biological fluid when said detected weight substantially equals said predetermined weight or is within said pre-determined weight range.

12. The method of claim 10 comprising adjusting a treatment parameter when said detected weight does not substantially equal said pre-determined weight or is outside said predetermined weight range.

13. The method of claim 10 comprising determining whether said biological fluid is treatment-ready by comparing the time of the detecting step relative to other events in a treatment.

14. The method of claim 10 comprising detecting the weight of said container at a pre-selected time of a treatment.

15. The method of claim 10 wherein said treatment comprises a treatment of a biological fluid with light.

16. The method of claim 15 comprising adjusting the duration of said light treatment in response to the detected weight of said container of biological fluid.

17. The method of claim 15 comprising adjusting the intensity of said light in response to the detected weight of said container of biological fluid.

18. The method of claim 15 comprising detecting said weight of said container of biological fluid to determine whether said biological fluid is treatment-ready.

19. The method of claim 18 wherein said detecting said weight of said container is an indication that said container has been prematurely placed in said treatment chamber.

20. The method of claim 10 further comprising generating an alert when said weight of said container does not substantially equal said pre-determined weight or is outside said predetermined weight range.

21. The method of claim 10 further comprising generating an alert when said container is not treatment ready or when said container has been prematurely placed in said treatment chamber.

* * * * *